US00PP36722P2

(12) United States Plant Patent
van Eijk

(10) Patent No.: US PP36,722 P2
(45) Date of Patent: Jun. 3, 2025

(54) ***AGAPANTHUS* PLANT NAMED 'FO21BM110'**

(50) Latin Name: ***Agapanthus* hybrid**
Varietal Denomination: FO21BM110

(71) Applicant: Bianca Theodora Helena van Eijk, Nootdorp (NL)

(72) Inventor: Bianca Theodora Helena van Eijk, Nootdorp (NL)

(73) Assignee: EIJCO B.V., Nootdorp (NL)

( * ) Notice: Subject to any disclaimer, the term of this patent is extended or adjusted under 35 U.S.C. 154(b) by 0 days.

(21) Appl. No.: 18/976,831

(22) Filed: Dec. 11, 2024

(30) Foreign Application Priority Data

Sep. 29, 2024 (QZ) ..... PBR 2024/2261

(51) Int. Cl.
*A01H 5/02* (2018.01)
*A01H 6/04* (2018.01)

(52) U.S. Cl.
USPC ..... Plt./398
CPC ..... *A01H 6/04* (2018.05)

(58) Field of Classification Search
USPC ..... Plt./398
CPC ..... A01H 6/04; A01H 5/02
See application file for complete search history.

*Primary Examiner* — Keith O. Robinson
(74) *Attorney, Agent, or Firm* — Penny J. Aguirre

(57) ABSTRACT

A new cultivar of *Agapanthus* plant named 'FO21BM110' that is characterized by its short leaves, its good shoot production, its floriferous habit with violet-blue flowers, and its short foliage height and relatively short peduncles.

2 Drawing Sheets

Botanical classification: *Agapanthus* hybrid.
Varietal denomination: 'FO21BM110'.

CROSS REFERENCE TO RELATED APPLICATIONS

This application claims priority to European Community Plant Variety Office (CPVO) Plant Breeder's Rights Application No. 2024/2261 filed Sep. 29, 2024 under 35 U.S.C. 119(f), the entire contents of which is incorporated by reference herein. The information for the plant breeders' rights application was received directly from the Inventor. This application is co-pending with a U.S. Plant Patent Application filed for plants derived from the same breeding program that is entitled *Agapanthus* Plant Named 'FO21WM111' (U.S. Plant patent application Ser. No. 18/976,959).

BACKGROUND OF THE INVENTION

The present invention relates to a new and distinct cultivar of *Agapanthus* of hybrid origin and will be referred to hereafter by its cultivar name, 'FO21BM110'. 'FO21BM110' represents a new perennial grown for landscape and container use.

The new cultivar was derived from a controlled breeding program by the Inventor in Pijnacker, Netherlands. The goal of the breeding program was to develop new cultivars of *Agapanthus* with a high production of flowering stems on short peduncles, short plant habits, and unique flowers. The Inventor collected seeds after open pollination in July of 2016 of unnamed and unpatented proprietary plants of *Agapanthus* from the Inventors' breeding program. The collected seeds were pooled before planting and therefore the exact parents are unknown. The Inventor selected 'FO21BM110' in June of 2017 as a single unique plant amongst the resulting seedlings.

Asexual propagation of the new cultivar was first accomplished by division by the Inventor in Pijnacker, Netherlands in July of 2019. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'FO21BM110' as a distinct cultivar of *Agapanthus*.

1. 'FO21BM110' exhibits short leaves.
2. 'FO21BM110' exhibits good shoot production.
3. 'FO21BM110' exhibits a floriferous habit with violet-blue flowers.
4. 'FO21BM110' exhibits a short foliage height and relatively short peduncles.

'FO21BM110' can be most closely compared to the *Agapanthus* cultivars 'Corag02Bl' (not patented), 'Ellen' (not patented), and 'FO21WM111'. 'Corag02Bl' is similar to 'FO21BM110' in having violet-blue flowers and short peduncles. 'Corag02Bl' differs from 'FO21BM110' in having more narrow leaves, shorter peduncles and plant height, less dense inflorescences, and flower buds that are darker violet-blue in color. 'Ellen' is similar to 'FO21BM110' in having violet-blue flowers and short peduncles. 'Ellen' differs from 'FO21BM110' in having leaves that are more narrow and darker violet-blue flower buds. 'FO21WM111' is similar to 'FO21BM110' in having short leaves and peduncles and dense flower heads. 'FO21WM111' differs from 'FO21BM110' in having white flowers and in commencing bloom earlier in the season.

BRIEF DESCRIPTION OF THE DRAWINGS

The accompanying color photographs illustrate the overall appearance and distinct characteristics of the new

*Agapanthus*. The photographs were taken of a plant 3 years in age of 'FO21BM110' as grown outdoors in a 23-cm container in Nootdorp, Netherlands.

Figure 1:
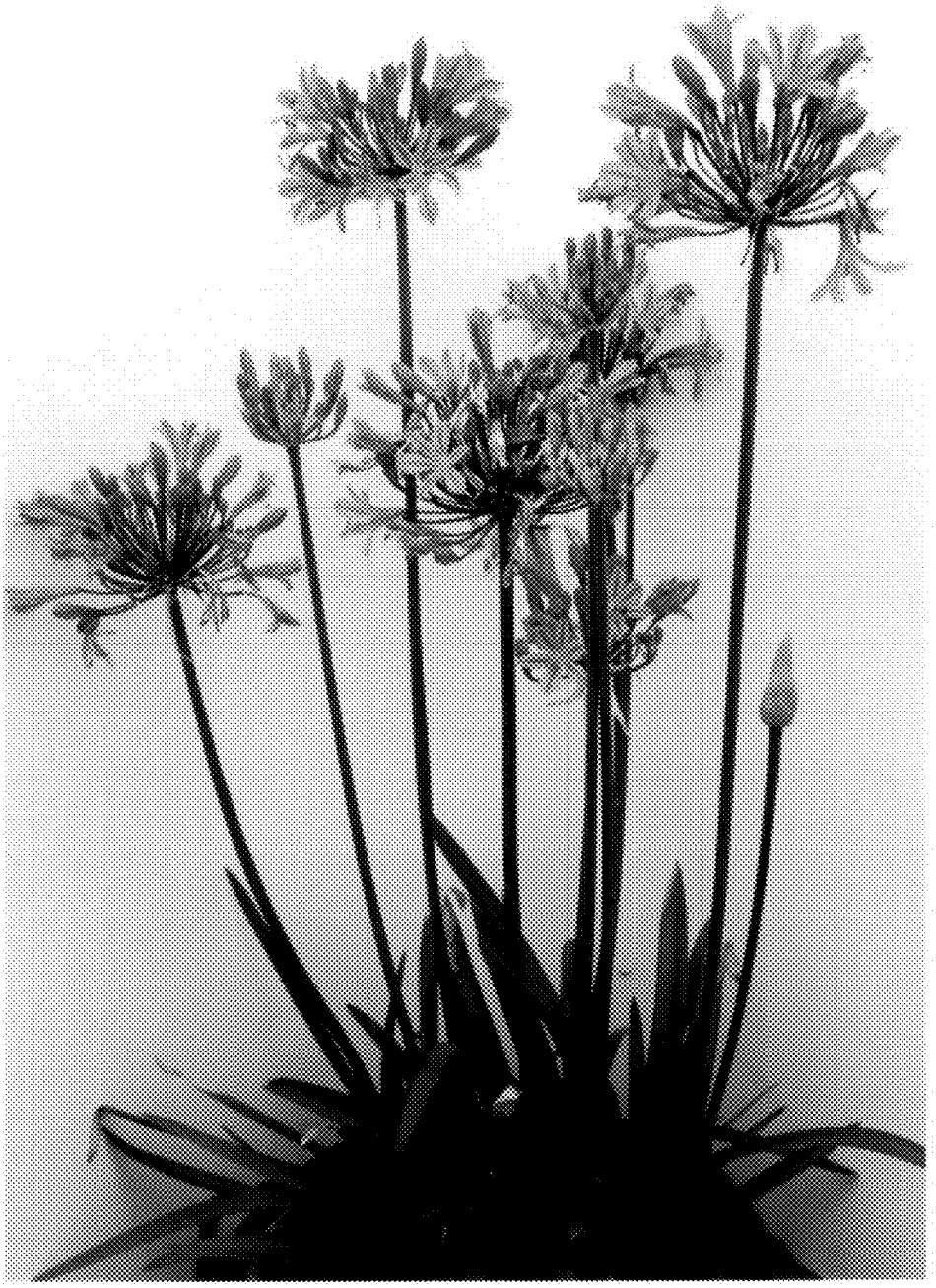

The photograph in FIG. 1 provides a side view of a plant of 'FO21BM110' in bloom.

Figure 2:
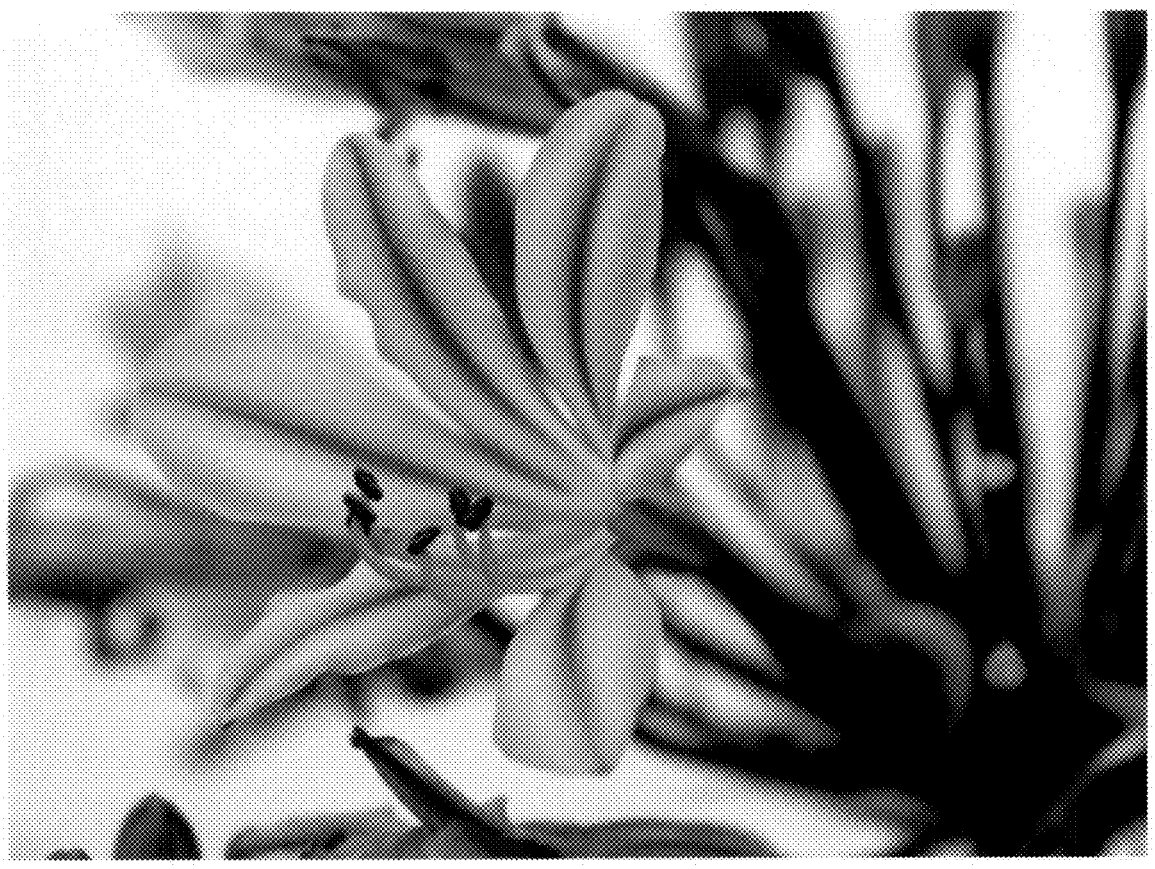

The photograph in FIG. 2 provides a close-up view of a flower of 'FO21BM110'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 3-year-old plants of 'FO21BM110' as grown outdoors in 23-cm containers in Nootdorp, Netherlands. The phenotype of the new cultivar may vary with variations in environmental, climatic, and cultural conditions, as it has not been tested under all possible environmental conditions. The color determinations are in accordance with The 2015 Colour Chart of The Royal Horticultural Society (2019 reprint), London, England, except where general color terms of ordinary dictionary significance are used.

General description:

*Blooming period*.—June through November in The Netherlands (climate dependent).

*Plant type*.—Semi-deciduous (climate dependent) herbaceous perennial.

*Plant habit*.—Basal rosettes with inflorescences emerging from the rosette center.

*Height and spread*.—An average of 34 cm in height from soil to top of foliar plane, 51.5 cm in height from soil level to top of floral plane, 68 cm in diameter as a 3-year-old plant grown in a container.

*Cold hardiness*.—At least to U.S.D.A. Zone 8.

*Diseases and pests*.—No resistance or susceptibility to diseases or pests has been observed.

*Root description*.—Thick and fleshy.

*Propagation*.—Division and Tissue culture (preferred).

*Time required for root development*.—Time for root initiation; between 3 to 10 weeks, time to produce a rooted cutting; 7 months.

*Growth rate*.—Moderately vigorous.

Foliage description:

*Leaf shape*.—Ligulate.

*Leaf division*.—Simple.

*Leaf base*.—Decurrent, broadly cuneate.

*Leaf arrangement*.—In basal rosettes, equitant.

*Leaf apex*.—Acute.

*Leaf aspect*.—Moderately carinate, slightly to moderately curved.

*Leaf venation*.—Parallel, upper and lower surface NN137B.

*Leaf margins*.—Entire.

*Leaf size*.—Average of 32.6 cm in length, 2.2 cm in width.

*Leaf surface*.—Smooth, glabrous, upper surface slightly glossy, lower surface very slightly glossy.

*Leaf number*.—Average of 10 leaves per rosette.

*Leaf color*.—Young leaves upper surface; 137B, young leaves lower surface; 143A and 143B, mature leaves upper surface; 137A and 137B, veins NN137A, mature leaves lower surface; 137B, veins NN137A and NN137B.

*Leaf attachment*.—Sessile to base.

Flower description:

*Inflorescence type*.—Umbel.

*Flower fragrance*.—None.

*Flower type*.—Flattened hemispherical.

*Flower number*.—An average of 60 flowers per umbel, flowers and buds per plant 240.

*Inflorescence size*.—Average of 10.5 cm in height, 14.5 cm in diameter.

*Flower size*.—An average of 4.2 cm in depth, 3.9 cm in diameter, throat is 3.5 mm in length, tube is 1.3 cm in length, 5 mm in diameter.

*Lastingness of inflorescence*.—Average of 2 weeks, self-cleaning.

*Flower aspect*.—Outwardly to upright.

*Peduncle*.—1 per rosette, strong, oval in shape, held primarily upright, surface is glabrous and smooth, moderately glossy, covered with a very thin waxy layer 145D in color, held in a 75° angle to soil level, average of 45.8 cm in length and 7.5 mm in width at the widest point and 5.5 mm at the narrowest point, a blend of 143B and 144A in color.

*Pedicels*.—Strong, average of 3.2 cm in length and 1.25 mm in width, held erect to outward in multiple angles, a blend of 143B and 144A in color, smooth and glabrous surface.

*Flower buds*.—Oblanceolate in shape, smooth, slightly velvety, slightly glossy surface, average of 2.5 cm in length and 6 mm in width, color; 91A, axially striped 92A, base 93C.

*Tepals*.—6, 2 whorls, oblanceolate in shape, lower tepals falcate, fused, entire margins, lower and upper tepals broadly acute, both surfaces are glabrous, slightly velvety, 4 cm in length, lower tepal 6.5 mm in width, upper tepal 9 mm in width, color: when opening upper surface; 91C, margins and top 91B, longitudinal central stripe N89D, when opening lower surface; a blend of 91A and 92B, margins and top 92A, longitudinal central stripe N89D, when fully open upper surface; 92C, margins and top 92B, longitudinal central stripe N89D, veins N89D, tepal fades to N81B and N81C, when fully open lower surface; 92B, longitudinal central stripe N89D, veins N89D, tepal fades to N81B and N81C, throat color; 92D, longitudinal central stripe N89D, veins N89D, tube color; 92B, axially striped 92A.

*Bracts*.—Immature inflorescence covered with 2 bracts, placed oppositely and dropped when individual flowers develop to open, broadly ovate in shape, average of 3.2 cm in length, 1.9 cm in width, color; upper surface 145D, veins 144A and 144B, lower surface 144B, top N77B, veins 148A, at the base of each individual pedicel, a single bract is present; filiform in shape, average of 2 cm in length and 1 mm in width, 155C in color.

Reproductive organs:

*Gynoecium*.—Pistil; 1, average of 2.8 cm in length, stigma; club-shaped, 1 mm in length, 0.5 mm in diameter, 91C in color, style; 2.7 cm in length, color; 91A, base 91D, ovary; 150D in color.

*Androecium*.—Stamens; 6, anthers; basifixed, oblong in shape, average of 2 mm in length, 1 mm in width, N187A in color, filament; 2.6 cm in length, color 91B and fading to N155A at the top, pollen; moderate in quantity and N199C in color.

*Fruit/seed*.—None observed to date.

It is claimed:

1. A new and distinct cultivar of *Agapanthus* plant named 'FO21BM110' as herein illustrated and described.

* * * * *